(12) United States Patent
Butler et al.

(10) Patent No.: US 10,188,801 B2
(45) Date of Patent: Jan. 29, 2019

(54) MECHANISM FOR PREVENTING SELECTION OF A DOSE

(75) Inventors: Joseph Butler, Warwickshire (GB); Richard James Vincent Avery, Chipping Camden (GB)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 276 days.

(21) Appl. No.: 13/813,477

(22) PCT Filed: Aug. 11, 2011

(86) PCT No.: PCT/EP2011/063841
§ 371 (c)(1),
(2), (4) Date: May 14, 2013

(87) PCT Pub. No.: WO2012/020085
PCT Pub. Date: Feb. 16, 2012

(65) Prior Publication Data
US 2013/0218095 A1  Aug. 22, 2013

Related U.S. Application Data

(60) Provisional application No. 61/373,386, filed on Aug. 13, 2010.

(30) Foreign Application Priority Data

Oct. 26, 2010 (EP) .................................. 10188849

(51) Int. Cl.
*A61M 5/315* (2006.01)
*A61M 5/24* (2006.01)

(52) U.S. Cl.
CPC .......... *A61M 5/31541* (2013.01); *A61M 5/24* (2013.01)

(58) Field of Classification Search
CPC .......... A61M 5/31541; A61M 5/31535; A61M 5/3156; A61M 5/3155; A61M 5/31593;
(Continued)

(56) References Cited

U.S. PATENT DOCUMENTS 533,575 A     2/1895  Wilkens
5,226,895 A   7/1993  Harris
(Continued)

FOREIGN PATENT DOCUMENTS

CN   101479000 A   7/2009
CN   101489607 A   7/2009
(Continued)

OTHER PUBLICATIONS

English Translation of Notice of Reasons for Rejection issued in Japanese Patent Application No. 2013-523617 dated Apr. 5, 2016.
(Continued)

*Primary Examiner* — Brandy S Lee
(74) *Attorney, Agent, or Firm* — McCarter & English, LLP

(57) ABSTRACT

A dose setting mechanism having a locking mechanism for preventing selection of a dose in a drug delivery device is disclosed. The dose setting mechanism includes a locking mechanism that prevents movement of the dose setting mechanism. When a correct cartridge is inserted into the drug delivery device, the locking mechanism unlocks so as to allow movement of the dose setting mechanism. In one arrangement, the locking mechanism prevents rotation of the dose setting mechanism.

20 Claims, 6 Drawing Sheets

(58) Field of Classification Search
CPC .......... A61M 5/31533; A61M 5/31525; A61M 5/24; A61M 5/31528; A61M 5/31536; A61M 5/31545; A61M 5/31571; A61M 5/50
USPC .................................................. 604/207, 209
See application file for complete search history.

(56) References Cited

U.S. PATENT DOCUMENTS

| | | | |
|---|---|---|---|
| 5,279,586 A | | 1/1994 | Balkwill |
| 5,304,152 A | | 4/1994 | Sams |
| 5,320,609 A | | 6/1994 | Haber et al. |
| 5,383,865 A | | 1/1995 | Michel |
| 5,480,387 A | | 1/1996 | Gabriel et al. |
| 5,505,704 A | | 4/1996 | Pawelka et al. |
| 5,582,598 A | | 12/1996 | Chanoch |
| 5,626,566 A | | 5/1997 | Petersen et al. |
| 5,674,204 A | | 10/1997 | Chanoch |
| 5,688,251 A | | 11/1997 | Chanoch |
| 5,921,966 A | | 7/1999 | Bendek et al. |
| 5,961,495 A | | 10/1999 | Walters et al. |
| 6,004,297 A | | 12/1999 | Steenfeldt-Jensen et al. |
| 6,045,537 A | * | 4/2000 | Klitmose ............ A61M 5/24 604/224 |
| 6,193,698 B1 | | 2/2001 | Kirchhofer et al. |
| 6,221,046 B1 | | 4/2001 | Burroughs et al. |
| 6,235,004 B1 | | 5/2001 | Steenfeldt-Jensen et al. |
| 6,248,095 B1 | | 6/2001 | Giambattista et al. |
| 6,277,098 B1 | * | 8/2001 | Klitmose ............ A61M 5/24 604/187 |
| 6,316,194 B1 | | 11/2001 | Karn et al. |
| 6,670,461 B1 | | 12/2003 | Wengel et al. |
| 6,858,846 B2 | | 2/2005 | Hjertman et al. |
| 6,899,698 B2 | | 5/2005 | Sams |
| 6,936,032 B1 | | 8/2005 | Bush, Jr. et al. |
| 7,241,278 B2 | | 7/2007 | Moller |
| 8,343,103 B2 | | 1/2013 | Moser |
| 8,734,403 B2 | | 5/2014 | Hirschel et al. |
| 9,050,397 B2 | | 6/2015 | Christiansen |
| 2002/0052578 A1 | | 5/2002 | Moller |
| 2002/0120235 A1 | | 8/2002 | Enggaard |
| 2003/0050609 A1 | | 3/2003 | Sams |
| 2004/0059299 A1 | | 3/2004 | Moller |
| 2004/0210199 A1 | | 10/2004 | Atterbury et al. |
| 2004/0267207 A1 | | 12/2004 | Veasey et al. |
| 2005/0113765 A1 | | 5/2005 | Veasey et al. |
| 2006/0153693 A1 | | 7/2006 | Fiechter et al. |
| 2009/0254027 A1 | * | 10/2009 | Moller ............ A61M 5/24 604/71 |
| 2009/0275916 A1 | | 11/2009 | Harms et al. |
| 2010/0010455 A1 | | 1/2010 | Elahi et al. |
| 2010/0042054 A1 | | 2/2010 | Elahi et al. |
| 2010/0106099 A1 | * | 4/2010 | Christiansen ....... A61M 5/3129 604/208 |

FOREIGN PATENT DOCUMENTS

| | | | | |
|---|---|---|---|---|
| CN | | 101511410 A | 8/2009 | |
| EP | | 0268191 A2 | 11/1988 | |
| EP | | 0937471 | 8/1999 | |
| EP | | 0937476 | 8/1999 | |
| JP | | 2000513967 A | 10/2000 | |
| JP | | 2009533094 A | 9/2009 | |
| JP | | 2009543631 A | 12/2009 | |
| JP | | 2010506603 A | 3/2010 | |
| JP | | 2010509963 A | 4/2010 | |
| WO | | 8808725 A1 | 5/1998 | |
| WO | | 99/38554 | 8/1999 | |
| WO | | 01/10484 | 2/2001 | |
| WO | | 2007115424 A1 | 10/2007 | |
| WO | | 2008009546 A1 | 1/2008 | |
| WO | | 2008009646 A1 | 1/2008 | |
| WO | | 2008009647 A1 | 1/2008 | |
| WO | WO 2008009646 A1 | * | 1/2008 | .............. A61M 5/24 |
| WO | | 2008019518 A1 | 2/2008 | |
| WO | | 2008059063 A1 | 5/2008 | |
| WO | | 2010006870 A1 | 1/2010 | |

OTHER PUBLICATIONS

Extended European Search Report issued in European Patent Application No. 10188849.3 dated Aug. 4, 2011.
English Translation of Second Office Action issued in Chinese Patent Application No. 201180049394.4 dated Mar. 16, 2015.
English Translation of Notice of Reasons for Rejection issued in Japanese Patent Application No. 2013-523617 dated Apr. 21, 2015.
English Translation of Notice of Reasons for Rejection issued in Japanese Patent Application No. 2013-523617 dated Aug. 25, 2015.

* cited by examiner

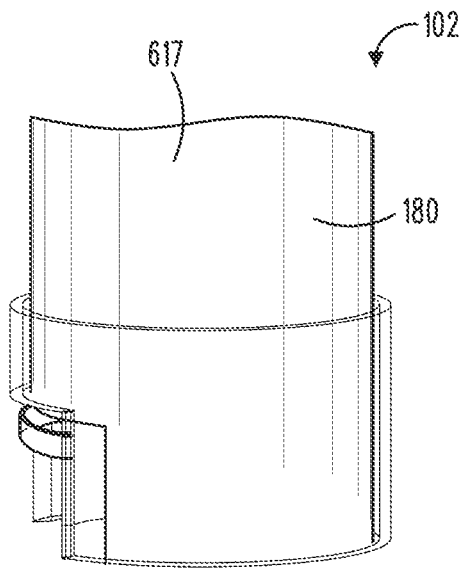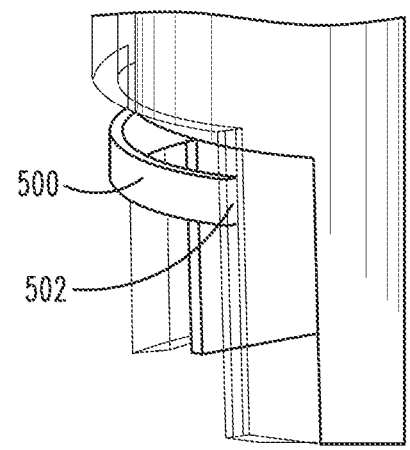
FIG. 9  FIG. 10
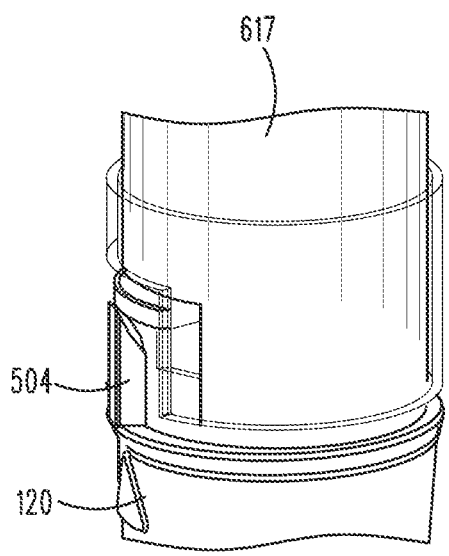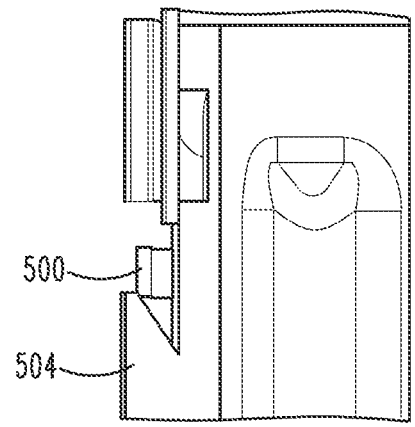
FIG. 11  FIG. 12

MECHANISM FOR PREVENTING SELECTION OF A DOSE

CROSS REFERENCE TO RELATED APPLICATIONS

The present application is a U.S. National Phase Application pursuant to 35 U.S.C. § 371 of International Application No. PCT/EP2011/063841 filed Aug. 11, 2011, which claims priority to U.S. Patent Application No. 61/373,386 filed Aug. 13, 2010 and European Patent Application No. 10188849.3 filed Oct. 26, 2010. The entire disclosure contents of these applications are herewith incorporated by reference into the present application.

FIELD OF INVENTION

Specific embodiments of the present disclosure relate to reservoirs, particularly reservoirs containing a medicament. More particularly, the present disclosure is generally directed to a mechanism for preventing selection of a dose for use with a reservoir and a reservoir holder so as to prevent unwanted reservoir cross use. As just one example, such medicament reservoirs may comprise an ampoule, a cartridge, a vial, or a pouch, and may be used with a medical delivery device. Exemplary medical delivery devices include, but are not limited to syringes, pen type injection syringes, pumps, inhalers, or other similar injection or infusing devices that require at least one reservoir containing at least one medicament.

BACKGROUND

Medicament reservoirs such as ampoules, cartridges, or vials are generally known. Such reservoirs are especially used for medicaments that may be self administered by a patient. For example, with respect to insulin, a patient suffering from diabetes may require a certain amount of insulin to either be injected via a pen type injection syringe or infused via a pump. With respect to certain known reusable pen type drug delivery devices, a patient may load a cartridge containing the insulin into a proximal end of a cartridge holder. After the cartridge has been correctly loaded, the user may then be called upon to select a dose of medicament. Multiple doses may be dosed from the cartridge. Where the drug delivery device comprises a reusable device, once the cartridge is empty, the cartridge holder may be disconnected from the drug delivery device and the empty cartridge may be removed and replaced with a new cartridge. Most suppliers of such cartridges recommend that the user may dispose of the empty cartridges properly. Where the drug delivery device comprises a disposable device, once the cartridge is empty, the user may be recommended to dispose of the entire device.

Such known self administration systems requiring the removal and reloading of empty cartridges have certain limitations. For example, in certain generally known systems, a user may simply load a new cartridge into the delivery system without the drug delivery device or without the cartridge having any mechanism of preventing cross use of an incorrect cartridge. That is, the drug delivery device does not have a mechanism for determining whether the medicament contained in the cartridge is indeed the correct type of medicament to be administered by the patient. Alternatively, certain known drug delivery devices do not present a mechanism for determining whether the correct type of medicament within the cartridge should be used with that particular drug delivery system. This potential problem could be exacerbated given that certain elderly patients, such as those suffering from diabetes, may have limited manual dexterity. Identifying an incorrect medicament is quite important, since the administration of a potentially incorrect dose of a medicament such as a short-acting insulin in lieu of a long-acting insulin could result in injury or even death.

Some drug delivery devices or systems may use a color coding scheme to assist a user or care giver in selecting the correct cartridge to be used with a drug delivery device. However, such color coding schemes pose challenges to certain users, especially those users suffering from poor eyesight or color blindness: a situation that can be quite prevalent in patients suffering from diabetes.

Another concern that may arise with such disposable cartridges is that these cartridges are manufactured in essentially standard sizes and must comply with certain recognized local and international standards. Consequently, such cartridges are typically supplied in standard sized cartridges (e.g. 3 ml cartridges). Therefore, there may be a variety of cartridges supplied by a number of different suppliers and containing a different medicament but fitting a single drug delivery device. As just one example, a first cartridge containing a first medicament from a first supplier may fit a medical delivery device provided by a second supplier. As such, a user might be able to load and then dispense an incorrect medicament (such as a rapid or basal type of insulin) into a reusable drug delivery device without being aware that the medical delivery device was perhaps neither designed nor intended to be used with such a cartridge.

As such, there is a growing desire from users, health care providers, care givers, regulatory entities, and medical device suppliers to reduce the potential risk of a user loading an incorrect drug type into a drug delivery device. There is also, therefore, a desire to reduce the risk of dispensing an incorrect medicament (or the wrong concentration of the medicament) from such a drug delivery device.

There is, therefore, a general need to physically dedicate or mechanically code a cartridge to its drug type and design an injection device that only accepts or works with the dedication or coded features provided on or with the cartridge so as to prevent unwanted cartridge cross use. Such injection device may comprise a reusable or a disposable drug delivery device. Similarly, there is also a general need for a dedicated cartridge that may allow the medical delivery device to be used with only an authorized cartridge containing a specific medicament while also preventing undesired cartridge cross use.

There is also a general need to provide a dedicated cartridge that is difficult to tamper with so that the cartridge may not be compromised in that the cartridge can be used with an unauthorized drug or drug delivery device. Because such cartridges may be difficult to tamper with, they may also reduce the risk of counterfeiting: i.e. making it more difficult for counterfeiters to provide unregulated counterfeit medicament carrying products.

The problem to be solved by the present invention is to provide a dose setting mechanism and a drug delivery system where the safety of the user is increased.

SUMMARY

One aspect relates to a dose setting mechanism. The dose setting mechanism may be for use with a drug delivery device. The dose setting mechanism may include a locking mechanism. The locking mechanism may be located at a distal end of the dose setting mechanism. The locking mechanism may prevent movement of a dose setter of the dose setting mechanism. The locking mechanism may prevent the dose setter from rotating. When a cartridge, in particular a correct cartridge, is inserted into the drug delivery device, the locking mechanism may be configured to unlock so as to allow relative movement of the dose setter.

A correct cartridge may be a cartridge comprising a mechanical coding corresponding to a mechanical coding of the locking mechanism, for example. A correct cartridge may comprise a medicament intended to be dispensed by means of the dose setting mechanism. In one arrangement, when the correct cartridge is inserted into the drug delivery device, the locking mechanism may unlock so as to allow rotation of the dose setter. The dose setting mechanism may comprise a reusable or a disposable dose setting mechanism.

According to an embodiment, the correct cartridge is a coded cartridge. The coded cartridge may comprise a mechanical coding, e.g. a protrusion. Said mechanical coding may correspond to a mechanical coding of the locking mechanism, e.g. an indentation. The coded cartridge may unlock the locking mechanism. Alternatively, a coded cartridge holder may unlock the locking mechanism. The coded cartridge holder may be adapted and arranged to receive a cartridge. The coded cartridge or the coded cartridge holder may comprise a protrusion.

According to an embodiment, the locking mechanism comprises at least one locking element. The locking mechanism may comprise at least one protrusion. The locking mechanism may comprise two or more locking elements. The locking mechanism may comprise two or more protrusions. The at least one locking element may move, in particular move in a proximal direction, to unlock the locking mechanism.

According to an embodiment, the locking mechanism comprises at least one locking pin. The locking mechanism may comprise two or more pins. The locking mechanism may comprise a gear. The at least one locking pin may move, in particular in a distal direction, to unlock the locking mechanism.

According to an embodiment, the locking mechanism comprises a first locking arm. The locking mechanism may comprise a second locking arm. The first and second locking arms may be provided on a pivoting hub.

According to an embodiment, the locking mechanism comprises a locking arm. The locking arm may comprise a pivotable locking arm. The pivotable locking arm may interact with a groove. The groove may be located on the dose setting mechanism. The locking arm may be positioned in a circumferential direction. In particular, the locking arm may be positioned circumferentially around a body of a drug delivery device comprising the locking mechanism.

According to an embodiment, the dose setting mechanism comprises a reusable dose setting mechanism. Alternatively, the dose setting mechanism may comprise a non-reusable dose setting mechanism.

A further aspect relates to a drug delivery system. The system may include a drug delivery device. The drug delivery device may be a pen type device, e.g. a pen type injector. The device may comprise a dose setting mechanism. The device may, for example, comprise the previously described dose setting mechanism. A cartridge may be contained within the dose setting mechanism. The device may comprise a locking mechanism. The locking mechanism may prevent a movement of a dose setter. When a correct cartridge is inserted into the drug delivery device, the locking mechanism may be configured unlock so as to allow the dose setter to set a dose. The dose setting mechanism may comprise a reusable or a disposable dose setting mechanism.

According to an embodiment, the locking mechanism locks to prevent the dose setter of the dose setting mechanism from rotating. When the correct cartridge is inserted into the drug delivery device, the locking mechanism may unlock to allow the dose setter to be rotated.

According to an embodiment, the drug delivery device comprises a cartridge holder. The cartridge holder may be securable to the dose setting mechanism. In particular, the cartridge holder may be permanently or releasably secured to the dose setting mechanism. A cartridge may be contained within the cartridge holder. The cartridge holder may have a coding. The coding may unlock the locking mechanism. Alternatively, a coded cartridge may unlock the locking mechanism. The coding may comprise a mechanical coding. The coding may comprise a protrusion.

According to an embodiment, the locking mechanism comprises a locking element. The locking mechanism may comprise two or more locking elements. The locking mechanism may comprise a protrusion. The locking mechanism may comprise two or more protrusion.

According to an embodiment, the locking mechanism comprises at least one locking pin. The locking mechanism may comprise two or more locking pins. The locking mechanism may comprise a gear.

According to an embodiment, the locking mechanism comprises a first locking arm. The locking mechanism may comprise a second locking arm. The first locking arm and the second locking arm may be provided on a pivoting hub.

According to an embodiment, the locking mechanism comprises a locking arm.

According to an embodiment, the drug delivery system comprises a reusable drug delivery system. Alternatively, the drug delivery system may comprise a non-reusable drug delivery system.

According to an embodiment, the drug delivery system further comprises a cartridge. The cartridge may be contained within the dose setting mechanism.

According to a preferred embodiment, a dose setting mechanism for use with a drug delivery device is provided, the dose setting mechanism comprising a locking mechanism configured to prevent movement of a dose setter. When a cartridge is inserted into the drug delivery device, the locking mechanism is configured to unlock so as to allow movement of the dose setter.

According to a preferred embodiment, a dose setting mechanism for use with a drug delivery device is provided, the dose setting mechanism comprising a locking mechanism that prevents movement of a dose setter. When a correct cartridge is inserted into the drug delivery device, the locking mechanism unlocks so as to allow movement of the dose setter.

According to a preferred embodiment, a drug delivery system is provided, the system comprising a drug delivery device comprising the previously described dose setting mechanism. The locking mechanism of the dose setting mechanism is configured to prevent a movement of a dose setter of the dose setting mechanism.

According to a preferred embodiment, a drug delivery system is provided, the system comprising a drug delivery device comprising a dose setting mechanism and a locking mechanism that prevents a movement of a dose setter of the dose setting mechanism. When a correct cartridge is inserted into the drug delivery device, the locking mechanism unlocks so as to allow the dose setter to be moved to set a dose.

These as well as other advantages of various aspects of the present invention will become apparent to those of ordinary skill in the art by reading the following detailed description, with appropriate reference to the accompanying drawings.

BRIEF DESCRIPTION OF THE DRAWINGS

Exemplary embodiments are described herein with reference to the drawings, in which:

FIG. 9 illustrates an alternate embodiment of the mechanism shown in FIG. 7;

FIG. 10 illustrates close-up view of the mechanism shown in FIG. 9;

FIG. 11 illustrates the mechanism shown in FIG. 9 in the unlocked position; and

FIG. 12 illustrates a side view of the mechanism shown in FIG. 11.

DETAILED DESCRIPTION

Figure 1A:
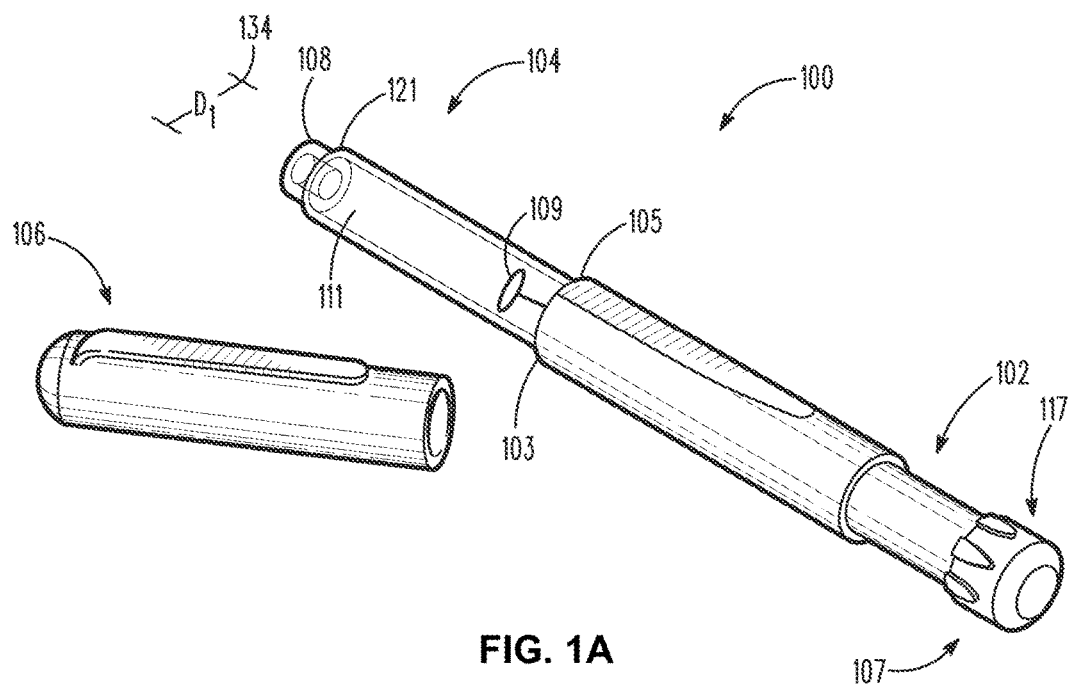
FIG. 1A illustrates an exemplary pen type drug delivery device.

Referring to FIG. 1A, there is shown a drug delivery device 100 in the form of a pen type syringe. This drug delivery device 100 comprises a dose setting mechanism 102, a cartridge holder 104, and a removable cap 106. A proximal end 105 of the cartridge holder 104 and a distal end 103 of the dose setting mechanism 102 are removably secured together. The pen type syringe may comprise a re-usable or a disposable pen type syringe. Where the syringe comprises a reusable device 100, the cartridge holder 104 and the dose setting mechanism 102 are removably coupled together. In a disposable device 100, they are permanently coupled together. In FIG. 1, the dose setting mechanism 102 comprises a piston rod 109, such as a threaded piston rod that rotates when a dose is injected.

To inject a previously set dose, a double ended needle assembly (not explicitly shown) is attached to a distal end 108 of the cartridge holder 104. Preferably, the distal end 108 of the holder 104 comprises a thread 121 (or other suitable connecting mechanism such as a snap lock, snap fit, form fit, or bayonet lock mechanism) so that the needle assembly may be removably attached to the distal end 108 of the holder 104. When the drug delivery device 100 is not in use, the removable cap 106 can be releasably retained over the cartridge holder 104.

Figure 1B:
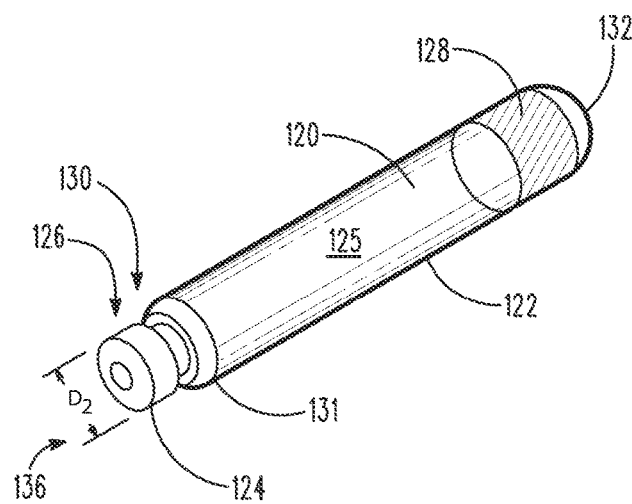
FIG. 1B illustrates a cartridge that may be loaded into a cartridge holder of the pen type drug delivery device illustrated in FIG. 1.

An inner cartridge cavity 111 defined by the cartridge holder 104 is dimensioned and configured to securely receive and retain a cartridge 120 (see FIG. 1B). In an alternate embodiment, the cartridge 120 is inserted directly into the drug delivery device 100 without the use of a cartridge holder 104. FIG. 1B illustrates a perspective view of the cartridge 120 that may be used with the drug delivery device 100 illustrated in FIG. 1A. The cartridge 120 includes a generally tubular barrel 122 extending from a distal end 130 to a proximal end 132. The distal end 130 is defined by an inwardly converging shoulder 131.

At the distal end 130, the cartridge 120 includes a smaller diameter neck 126 and this neck 126 projects distally from the shoulder 131 of the barrel 122. Preferably, this smaller diameter neck 126 is provided with a large diameter annular bead and this bead extends circumferentially thereabout at the extreme distal end of the neck 126. A pierceable seal or septum 1000 is securely mounted across the open distal end defined by the neck. The seal 1000 may be held in place by a metallic sleeve or ferrule 124. This ferrule 124 may be crimped around the circumferential bead at the distal end of the neck 126. A medicament 125 is pre-filled into the cartridge 120 and is retained within the cartridge 120, in part, by the pierceable seal 1000, the metallic sleeve 124, and a stopper 128.

The term "medicament", as used herein, preferably means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(30) human insulin and B29-N-(ω-carboxyhepta-decanoyl) human insulin.

Exendin-4 for example means Exendin-4(1-39), a peptide of the sequence H His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser- Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;

or an Exendin-4 derivative of the sequence
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2) 25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2) 25, Asp28] Exendin-4(1-39)-(Lys)6-NH2;
or a pharmaceutically acceptable salt or solvate of any one of the aforementioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1 C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

The stopper 128 is in sliding fluid-tight engagement with the inner tubular wall of the barrel 122. Axially directed forces acting upon the stopper 128 during dose injection or dose administration urges the medication 125 from the cartridge 120 though the double ended needle mounted onto the distal end 130 of the cartridge holder 104 and into the injection site. Such axial forces may be provided by the piston rod 109.

A portion of the cartridge holder 104 defining the cartridge holder cavity 111 is of substantially uniform diameter represented in FIG. 1A by D1 134. This diameter D1 134 is preferably slightly greater than a diameter D2 136 of the cartridge 120. The interior of the cartridge holder 104 includes an inwardly-extending annular portion or stop that is dimensioned to prevent the cartridge 120 from moving within the cartridge holder 104. In this manner, when the cartridge 120 is loaded into the cavity 111 of the cartridge holder 104 and the cartridge holder 104 is then connected to the dose setting member or dose setting mechanism 102, the cartridge 120 will be securely held within the cartridge cavity 111. More particularly, the neck 126 and ferrule 124 of the cartridge 120 are inserted in a proximal to distal direction into the open proximal end of the cartridge holder 104 with the ferrule 124 eventually passing entirely into the holder 104. With the holder 104 removably coupled to the dose setting mechanism 102, the proximal end of the cartridge 120 will typically abut a stop provided by the dose setting member 102.

A number of doses of the medicament 125 may be dispensed from the cartridge 120. Preferably, the cartridge 120 contains a type of medicament 125 that must be administered often, such as one or more times a day. One such medicament 125 is insulin. The movable stopper or piston 128 is retained in a first end or proximal end of the cartridge 120 and receives the axial force created by the piston rod 109 of the dose setting mechanism 102 as described above.

The dose setting mechanism 102 comprises a dose setter 117 (see FIG. 1A) at a proximal end 107 of the dose setting mechanism 102. In one preferred arrangement, the dose setter 117 may extend along the entire length of the dose setting mechanism 102 and may be a rotatable dose setter. However, alternative dose setter arrangements may also be used. For example, rather than rotate, these alternative dose setters 117 may be manipulated differently in order to set a dose, e.g. such alternative dose setters 117 may be pulled in the proximal direction or alternatively may be pulled and/or twisted in one or more directions in order to set a dose.

In a preferred arrangement, the dose setter 117 may be manipulated by a user so as to set a dose. As will be described in greater detail below, various locking mechanism embodiments are disclosed that will prevent a movement of the dose setter 117 (e.g. preventing rotation) when an incorrect cartridge 120 is inserted into the device 100 and, thereby, prevent the dose setter 117 from setting a dose.

To administer a dose that may be set by manipulating the dose setter 117, the user attaches the needle assembly comprising the double ended needle on the distal end 108 of the cartridge holder 104. In this manner, the needle assembly pierces the seal 1000 of the cartridge 120 and is, therefore, in liquid communication with the medicament 125. The user pushes on the dose setter 117 to inject the set dose. The same dose setting and dose administration procedure is followed until the medicament 125 in the cartridge 120 is expended and then a new cartridge must be loaded in the device 100. To exchange an empty cartridge 120, the user is called upon to remove the cartridge holder 104 from the dose setting mechanism 102.

Figure 2:
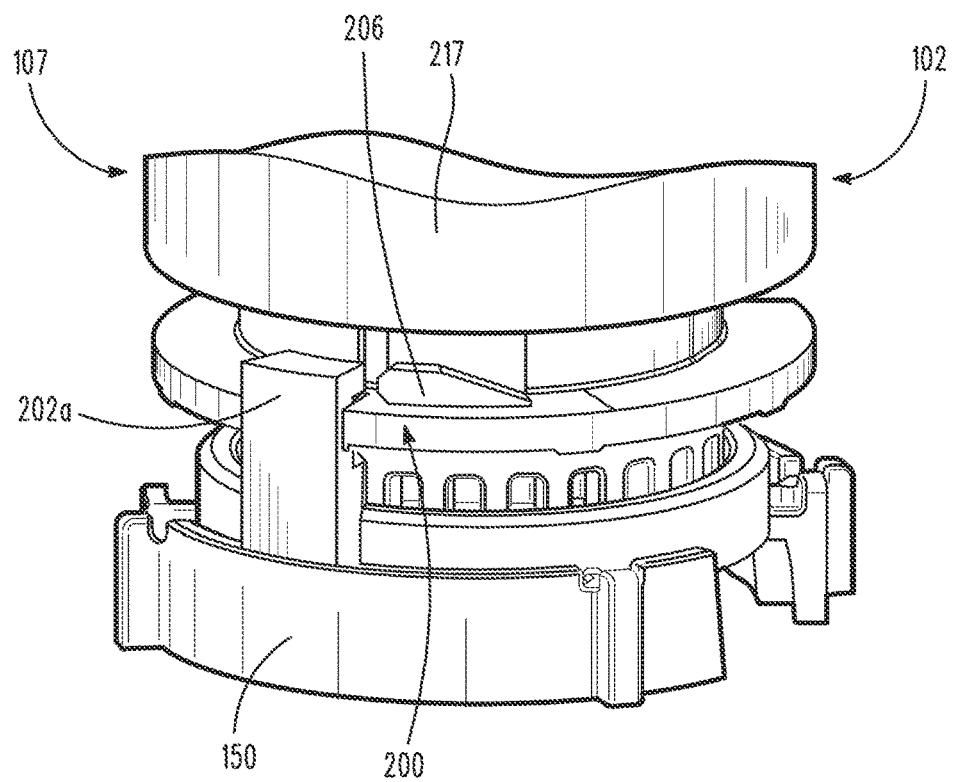
FIG. 2 illustrates a first embodiment of a mechanism for preventing selection of a dose for use with a cartridge that may be used with a pen type drug delivery device, such as the drug delivery device illustrated in FIG. 1.

FIG. 2 illustrates a first embodiment of a dose setting mechanism 102 that has a locking mechanism. This locking mechanism prevents selection of a dose by preventing a user from rotating the dose setter 117 if an incorrect cartridge 120 is inserted into the device 100. This dose setting mechanism 102 may be used with a cartridge 120 or cartridge holder 104, and may be used with a pen type drug delivery device, such as the drug delivery device 100 illustrated in FIG. 1A. The locking mechanism ensures that the correct cartridge 120 is used with the correct cartridge holder 104 and drug delivery device 100.

In one preferred arrangement, coding features may be located on the cartridge 120 or holder 104, and corresponding coding features may be located on the cartridge holder 104 or the drug delivery device 100. If the coding features do not mate, rotation of the dose setting mechanism 102 is prevented by the locking mechanism and, thus, the user is alerted that the medicament or drug 125 contained within the cartridge 120 is incorrect. In addition to ensure the correct drug type, the device 100 may also check other details, e.g. expiry date of the drug.

A first coding feature (not shown) may be located on either the cartridge 120 or on an interface component that fits on the cartridge 120. The first coding feature may include one or more protrusions, for example. The protrusions may be of different sizes and shapes, or there may be any number of protrusions, grooves, or different features. A corresponding second coding feature, such as one or more grooves or indentations, may be on a locking element located within the cavity of the drug delivery device 100. Thus, the first coding feature may cooperate with the second coding feature to mechanically code the cartridge 120 or a separate interface component to the locking element.

FIG. 2 shows a close-up view of an exemplary dose setting mechanism 102 comprising an outer body (not shown so that inner components can be seen), a rotatable dose setter 217, and a locking ring 150. The dose setting mechanism 102 may also include a locking mechanism 200 located toward the distal end 107. In FIG. 2, this locking mechanism 200 resides in a first or locked position, and the mechanism 200 may be normally biased into this state by a spring (not explicitly shown). This locking mechanism 200 prevents relative movement of the dose setter 217 e.g. rotation) and, hence, prevents selection of a dose when locked.

Figure 3:
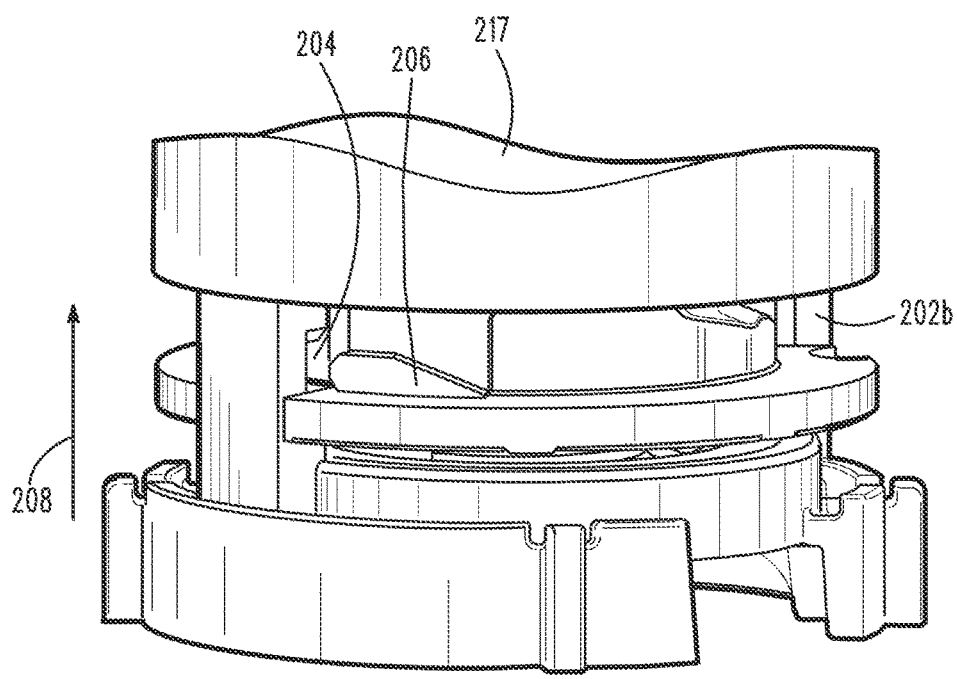
FIG. 3 illustrates the mechanism shown in FIG. 2 in the unlocked position.

The locking mechanism 200 may include a first movable locking element 202a that comprises a slot 204 (see FIG. 3). The first movable locking element 202a resides in a second position or an unlocked position and this may best be seen in FIG. 3. The first locking element 202a may be supported by the body of the drug delivery device 100 so as to limit stresses and so that the locking element 202a is loaded mainly in shear with negligible bending. Alternatively, a plurality of locking elements may be used to increase strength. The plurality of locking elements may be spaced equally apart. For example, a second locking element 202b is illustrated in FIG. 3. The locking mechanism 200 may further include a protrusion 206 and this protrusion 206 may reside along a distal end of the dose setter 217. This protrusion 206 is shaped to interact with the first locking element 202a. Alternatively, a plurality of protrusions 206 may be incorporated. As just one example, a second protrusion 206 may be shaped to interact with the second locking element 202b. The size and shape of the protrusion 206 allows it to rotate on a helical path without contacting the edges of slot 204.

In a locked position, shown in FIG. 2, the slot 204 of the locking element 202a is not in alignment with the protrusion 206. As such, in this first locking position, the locking element 202a prevents the dose setter 217 of the dose setting mechanism 102 from rotating and, thereby, prevents a user from setting a dose with the dose setting mechanism 102.

In the unlocked position, shown in FIG. 3, when a coded cartridge, such as cartridge 120, is inserted into the drug delivery device 100, a coding on the cartridge 120 pushes on the locking ring 150, and so moves the locking ring 150 in a proximal direction 208. The slot 204 of the locking element 202a is then exposed (as illustrated in FIG. 3), thereby enabling the protrusion 206 to pass through the slot 204 as the dose setter 217 is rotated. Therefore, the dose setter 217 of the setting mechanism 102 is now free to rotate so as to allow a user to set a dose. If the coding on the cartridge 120 does not match with the coding on the locking ring 150, then either the locking ring 150 will not be actuated, or the coding will provide interference so as to prevent the assembly of the cartridge 120 onto the dose setting mechanism 102.

A visual indicator may also be included on the drug delivery device 100 to indicate to a user the state of the locking mechanism 200, i.e. whether the locking mechanism 200 is in a locked or unlocked position. For example, colored indicators, such as red when locked and green when unlocked, may be located on the drug delivery device 100 (not explicitly shown).

The coding features may be detected by electro-mechanical means, e.g. microswitches, or optical/magnetic switches. Dose selection could then be controlled electronically or electro-mechanically. For example, the user interface could prevent the user from selecting a dose electronically if an incorrect cartridge 120 is inserted, or an electro-mechanical mechanism such as a solenoid could physically prevent manual movement of the dose setter 117, 217.

Additionally, in one embodiment the coding may block all incorrect drugs 125. Thus, an incorrectly coded cartridge 120 that is inserted into the drug delivery device 100 would prevent the dose setting mechanism 102 from rotating so as to allow a user to set a dose by rotating the dose setter 117, 217. In another arrangement, the coding may block only certain types of medicament 125, e.g. a short-acting drug can be fitted into a drug delivery device intended for long-acting drugs, or a low concentration drug into a drug delivery device for high concentration, but not vice versa.

The locking mechanism 200 shown in FIGS. 2 and 3 can be configured to prevent dose selection if a zero dose is selected before inserting a cartridge assembly. An additional mechanism (not shown) could ensure that a cartridge assembly can only be inserted when the dose setting mechanism 102 resides in a zero dose position. That is, where the dose setter 117, 217 of the dose setting mechanism 102 is dialed in or manipulated all the way to a distal stop position.

In an alternative embodiment (not shown), the dose setter 117, 217 could be prevented from rotating even if a zero dose is not selected before inserting a cartridge assembly. With the correct cartridge 120, an inwardly directed radial pin attached to the locking element 202a, 202b may follow a helical groove on the dose setting mechanism 102. With an incorrect drug 125, the radial pin may fall into one of a number of slots extending in an axial direction from the helical groove, and prevent rotation of the dose setter 117, 217.

Alternatively, the locking element 202a, 202b may incorporate features (not shown) to activate the dose setting mechanism 102 when a user inserts a correct cartridge 120. For example, the locking element 202a, 202b may be attached to a leadscrew nut (not explicitly shown) which prevents both dose selection and dispensing if an incorrect cartridge 120 is installed.

Figure 4:
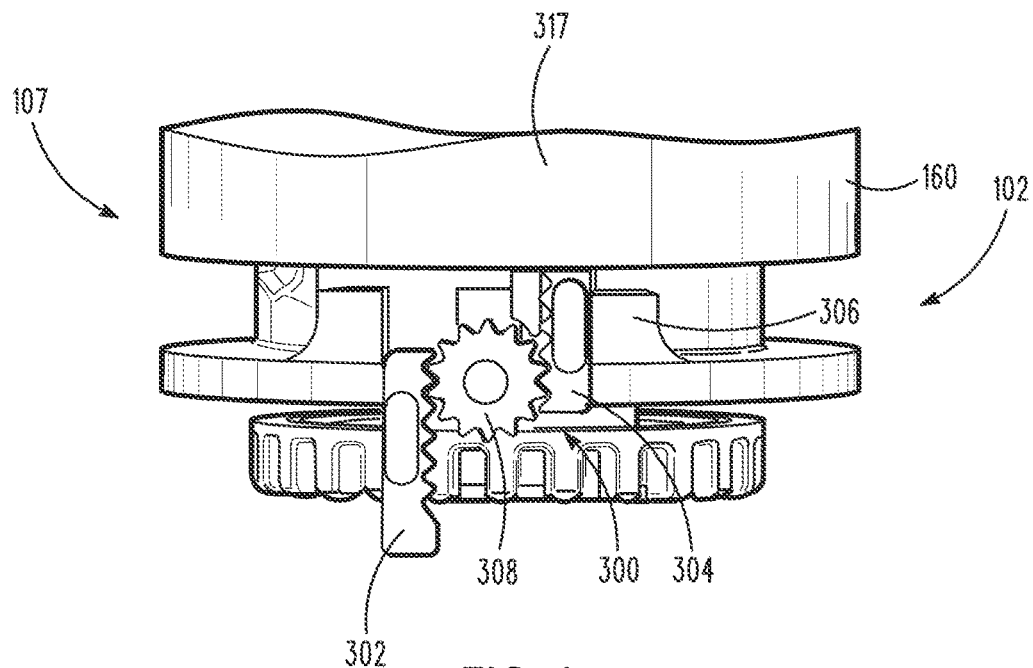
FIG. 4 illustrates a second embodiment of a mechanism for preventing selection of a dose for use with a cartridge that may be used with a pen type drug delivery device, such as the drug delivery device illustrated in FIG. 1.
Figure 5:
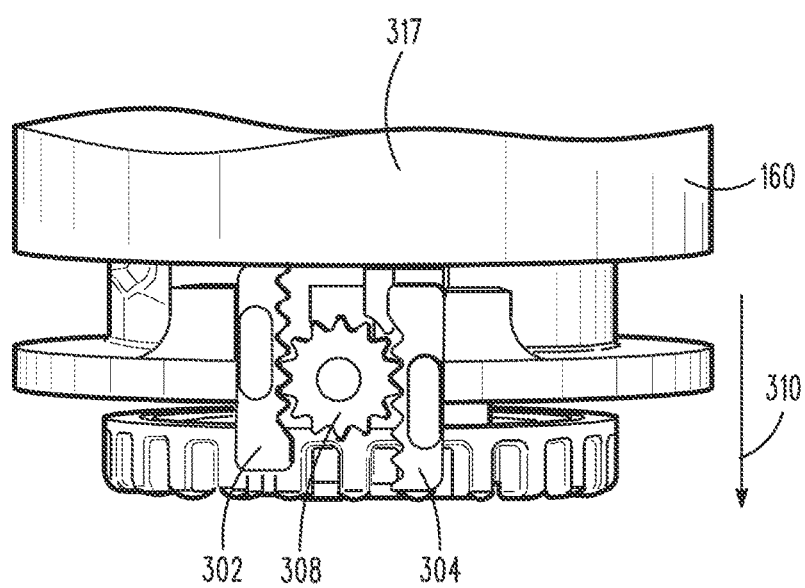
FIG. 5 illustrates the mechanism shown in FIG. 4 in the unlocked position.
Figure 6:
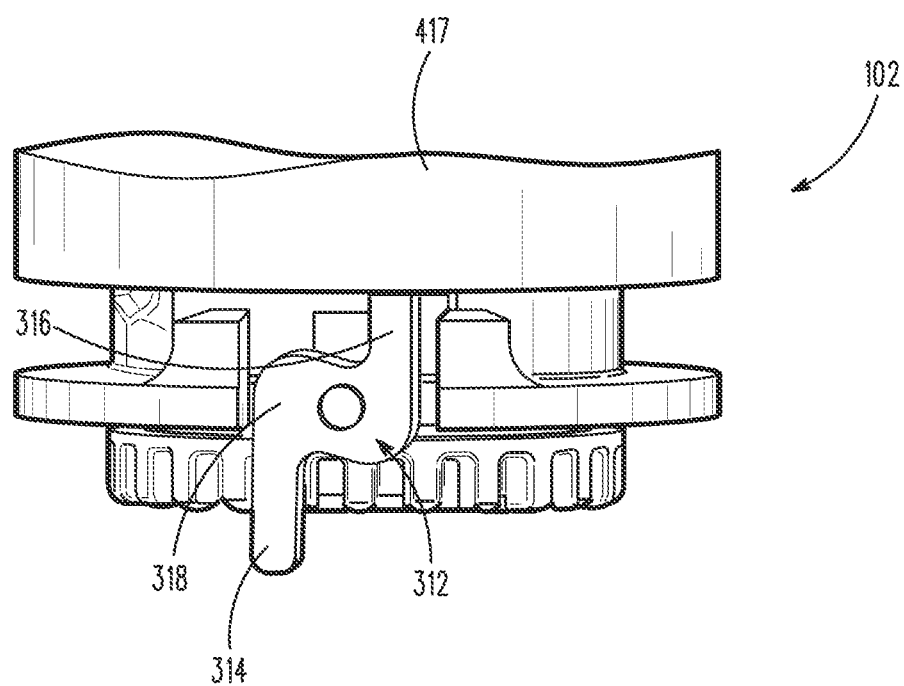
FIG. 6 illustrates an alternate embodiment of the mechanism shown in FIG. 4.

In another embodiment, shown in FIGS. 4-6, the dose setting mechanism 102 comprises a dose setter 317 that has a cylindrical section 160 located at the distal end 107. The dose setting mechanism 102 may include a locking mechanism 300 located toward the distal end 107 that prevents selection of a dose when locked.

The locking mechanism 300 may include a first pin 302 and a second pin 304. The first and second pins 302, 304 may attach to the body of the dose setting mechanism 102. As a spur gear 308 rotates, the pins 302, 304 may interact with the spur gear 308. The pins 302, 304 may move along the spur gear 308 in opposite directions to lock and unlock the locking mechanism 300.

In a locked position, shown in FIG. 4, the second pin 304 resides within an opening (not shown) in the cylindrical section 160 to lock rotation of the dose setter 317. Dose selection may be normally locked to prevent use of uncoded cartridges 120, or for safety in case of system failure.

In the unlocked position, shown in FIG. 5, when a coded cartridge or holder, such as cartridge 120 or holder 104, is inserted into the drug delivery device 100, the cartridge 120 or holder 104 pushes on the first pin 302 in a proximal direction, which in turn rotates the spur gear 308 in the clockwise direction. As such, the second pin 304 is then released from the cylindrical section 160 and moves in a distal direction 310. Therefore, the dose setter 317 is free to rotate. If the coding on the cartridge 120 does not match with the coding on the locking pin 302, 304, then either the locking pin 302, 304 will not be actuated, or the coding will provide interference so as to prevent assembly of the cartridge 120 onto the dose setting mechanism 102.

In an alternate embodiment of a dose setter 417 shown in FIG. 6, the pins 302, 304 and spur gear 308 may be replaced by a single piece 312. This single piece 312 comprises a first and a second locking arm 314, 316 provided on a pivoting hub 318. This single piece 312 may be molded from a flexible material so that the locking arms 314, 316 can bend as a central boss pivots.

Figure 7:
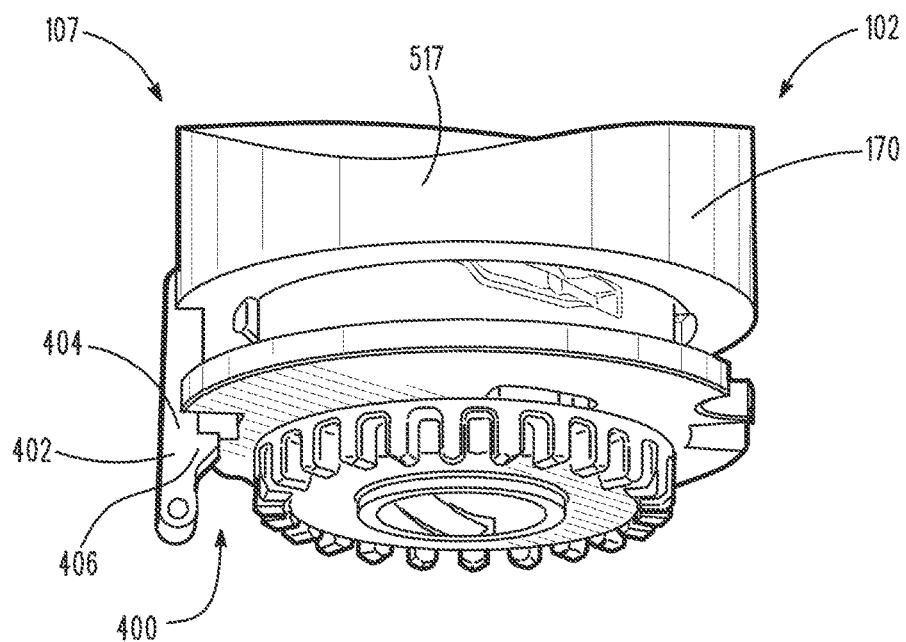
FIG. 7 illustrates a third embodiment of a mechanism for preventing selection of a dose for use with a cartridge that may be used with a pen type drug delivery device, such as the drug delivery device illustrated in FIG. 1.
Figure 8:
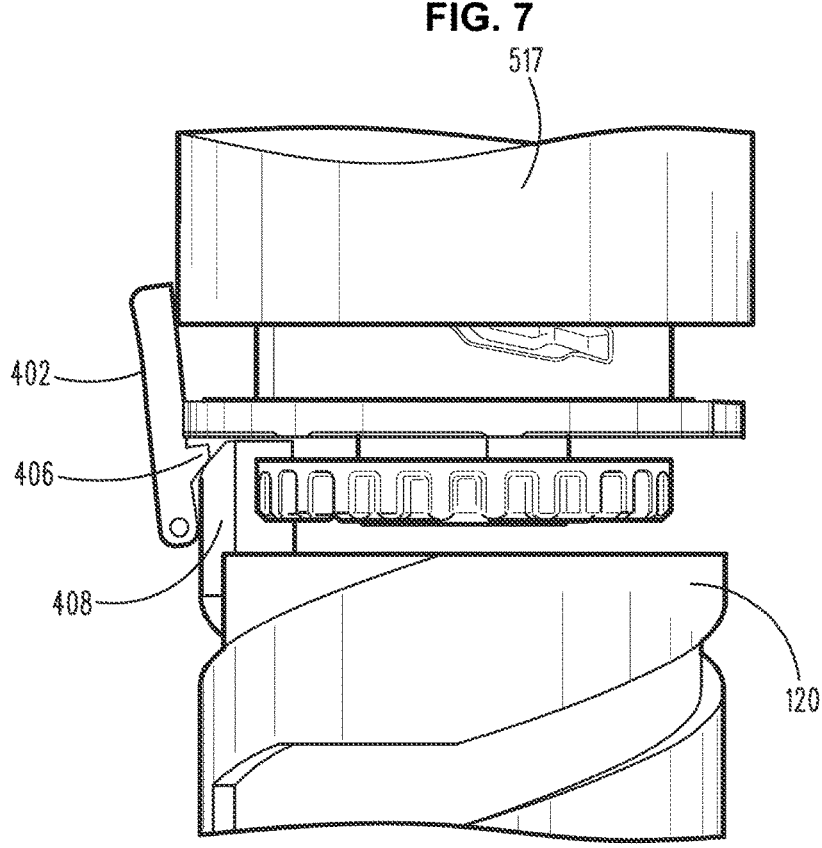
FIG. 8 illustrates the mechanism shown in FIG. 7 in the unlocked position.

FIGS. 7-8 show yet another example embodiment of a locking mechanism 400 located on a dose setting mechanism 102. In this embodiment, the dose setting mechanism 102 includes a cylindrical portion 170 at the distal end 107. A dose setter 517 is rotated to set the dose of medicament 125. The dose setting mechanism 102 may also include the locking mechanism 400 located toward the distal end 107 that prevents selection of a dose when locked.

The locking mechanism 400 may include a pivotable locking arm 402 that is normally biased by a spring into engagement with a groove 404 located on the cylindrical portion 170. The locking arm 402 may further include a cam 406 that protrudes outwardly from the pivotable locking arm 402. The locking arm 402 may be manufactured from a resilient material. The pivotable locking arm 402 may alternatively pivot about a longitudinal axis. In other words, the pivotable locking arm 402 could be perpendicular to the arm illustrated in FIGS. 7 and 8, but would operate in the similar manner. A coded cartridge 120 having a coding feature, such as protrusion 408 (see FIG. 8), may be inserted into the drug delivery device 100 to unlock the locking mechanism 400.

In a locked position, shown in FIG. 7, the pivotable locking arm 402 is engaged within a groove 404 on the cylindrical portion 170 so as to prevent rotation of the dose setter 517.

In the unlocked position, shown in FIG. 8, when a coded cartridge, such as cartridge 120 having the protrusion 408, is inserted into the drug delivery device 100, the protrusion 408 pushes on the cam 406 of the pivotable locking arm 402 to pivot or tilt the locking arm 402 away from the groove 404 located in the cylindrical portion 170. Thus, the dose setter 517 is free to rotate.

In an alternative embodiment, the locking arm may be located on the cylindrical portion, as shown in FIGS. 9-12. In this embodiment, the cylindrical portion 180 includes a locking arm 500 positioned in a circumferential direction. In the locked position, as shown in FIGS. 9 and 10, the locking arm 500 contacts the body of the drug delivery device 100 at location 502 so as to prevent the rotation of a dose setter 617. In the unlocked position, shown in FIGS. 11 and 12, when a correctly coded cartridge 120 (or cartridge holder 104) is inserted into the drug delivery device 100, a coding, such as a protrusion 504, located on the cartridge 120 or cartridge holder 104 pushes inwardly on the locking arm 500. Thus, the locking arm 500 no longer contacts the body of the drug delivery device 100 and the dose setter 617 is free to rotate.

In yet another embodiment, electronic means may be used to read coding about the cartridge contents, and only enable dose selection with a correct and/or valid drug 125. In this embodiment, the coding feature may be in the form of mechanical features, read for example by optical switches or micro switches. Alternatively, the coding may be electronic, e.g. magnetic switches, RFID.

If the dose selection is electronic, e.g. by means of buttons, it can be prevented electronically. If dose selection is mechanical, it can be prevented by electro-mechanical means, e.g. a locking pin activated by a solenoid. The pin may lock into a hole or groove to prevent translation or rotation of a sleeve, or release a mechanical lock (for example a spring loaded locking arm), or activate any of the other embodiments.

In other situations, the disclosed dose setting mechanism 102 may apply to any drug delivery device, with any type of reservoir or primary pack, e.g. inhaler, pouch.

The disclosed dose setting mechanism 102 results in a number of advantages. For example, the disclosed dose setting mechanism 102 assists a user to distinguish between medicaments 125, thereby helping to ensure that a delivery device 100 can only be used with a medicament 125 for which the device 100 is intended. Therefore, with the disclosed dose setting mechanism 102 used with a coded cartridge 120, the cartridge 120 is prevented from being loaded into any other drug delivery device by loading the cartridge with an incorrect or unwanted interface. The disclosed cartridge coding and dose setting mechanism 102 prevents a user from completing one or more of the following actions: fully inserting the cartridge 120 into an incorrect cartridge holder or attaching the cartridge 120 and/or cartridge holder 104 onto an incorrect dose setting mechanism; rotating the dose setting mechanism 102 when an incorrect cartridge is inserted.

The disclosed dose setting mechanism 102 also results in a low cost mechanism since the system does not require a large number of parts and can be manufactured in a cost effective manner. Moreover, there are quite a large number of different coding configurations between the interface and the cartridge holder 104 that may be used. Consequently, with the disclosed dose setting mechanism 102, a large number of medicaments 125 can be distinguished from one another. In addition, with the disclosed dose setting mechanism 102, if a user attempts to load an incorrect reservoir or cartridge into a cartridge holder 104 designed for a different cartridge, the user will be alerted at an early stage of the assembly process.

Exemplary embodiments of the present invention have been described. Those skilled in the art will understand, however, that changes and modifications may be made to these arrangements without departing from the true scope and spirit of the present invention, which is defined by the claims.

The invention claimed is:

1. A dose setting mechanism for use with a drug delivery device, the dose setting mechanism comprising:
   a dose setter for selecting a dose; and
   a locking mechanism configured to prevent movement of the dose setter and selection of the dose,
   wherein the locking mechanism is configured such that inserting a correct cartridge into the drug delivery device unlocks the locking mechanism so as to allow movement of the dose setter and selection of the dose, and
   wherein the locking mechanism is configured such that inserting an incorrect cartridge into the drug delivery device locks the locking mechanism so as to prevent the dose setter from setting a dose, wherein the locking mechanism prevents the dose setter from rotating, and wherein, when the correct cartridge is inserted into the drug delivery device, the locking mechanism unlocks so as to allow the dose setter to rotate.

2. The dose setting mechanism of claim 1, wherein the correct cartridge comprises a coded cartridge that unlocks the locking mechanism, or wherein a coded cartridge holder unlocks the locking mechanism.

3. The dose setting mechanism of claim 2, wherein the coded cartridge comprises a protrusion.

4. The dose setting mechanism according to claim 1, wherein the locking mechanism comprises at least one locking element and at least one protrusion, wherein the at least one locking element moves in a proximal direction to unlock the locking mechanism.

5. The dose setting mechanism according to claim 1, wherein the locking mechanism comprises at least one locking pin and a gear, wherein the at least one locking pin moves in a distal direction to unlock the locking mechanism.

6. The dose setting mechanism according to claim 1, wherein the locking mechanism comprises a first and a second locking arm provided on a pivoting hub, wherein the locking arms are configured to bend as the hub pivots.

7. The dose setting mechanism according to claim 1, wherein the locking mechanism comprises a locking arm.

8. The dose setting mechanism of claim 7, wherein the locking arm comprises a pivotable locking arm configured to interact with a groove located on the dose setting mechanism.

9. The dose setting mechanism of a claim 7, wherein the locking arm is positioned in a circumferential direction.

10. A drug delivery system, the system comprising: a drug delivery device comprising the dose setting mechanism according to claim 1, wherein the locking mechanism of the dose setting mechanism is configured to prevent a movement of the dose setter of the dose setting mechanism.

11. The drug delivery system of claim 10, further comprising a cartridge holder secured to the dose setting mechanism, a cartridge being contained within the cartridge holder, and the cartridge holder having a coding that unlocks the locking mechanism.

12. The drug delivery system according to claim 10, wherein the coding comprises a protrusion.

13. The drug delivery system according to claim 10, wherein the drug delivery system comprises a reusable drug delivery system or a non-reusable drug delivery system.

14. The drug delivery system according to claim 10, wherein the drug delivery system further comprises a cartridge contained within the dose setting mechanism.

15. A dose setting mechanism for use with a drug delivery device, the dose setting mechanism comprising:
   a body
   a dose setter for selecting a dose; and
   a locking mechanism configured to prevent movement of the dose setter and selection of the dose,
   wherein the locking mechanism comprises a movable locking element supported by the body, mechanically engageable with the dose setter, and movable between a first position and a second position, wherein, when in the first position, the movable locking element prevents the dose setter from rotating relative to the body, and wherein when the movable locking element is in the second position the dose setter is free to rotate relative to the body, and
   wherein the locking mechanism is configured such that inserting a correct cartridge into the drug delivery device moves the movable locking element from the first position into the second position to unlock the locking mechanism and to allow movement of the dose setter and selection of the dose.

16. The dose setting mechanism according to claim 15, wherein the locking mechanism is configured such that inserting an incorrect cartridge into the drug delivery device keeps the movable locking element in the first position.

17. The dose setting mechanism according to claim 15, further comprising a spring configured to bias the movable locking element in the first position.

18. The dose setting mechanism according to claim 15, further comprising a movable locking ring comprising a locking ring coding and connected to the movable locking element, the locking ring being movable relative to the body between a distal position and a proximal position such that the movable locking element is in the first position when the locking ring is in the distal position and such that the movable locking element is in the second position when the locking ring is in the proximal position.

19. The dose setting mechanism according to claim 18, wherein the locking ring is configured to be moved from the distal axial position into the proximal axial position only by a cartridge coding matching with the locking ring coding.

20. A drug delivery system, the system comprising: a drug delivery device comprising the dose setting mechanism according to claim 15, wherein the locking mechanism of the dose setting mechanism is configured to prevent a movement of the dose setter of the dose setting mechanism.

\* \* \* \* \*